United States Patent [19]

Wozencroft

[11] Patent Number: 5,562,633
[45] Date of Patent: Oct. 8, 1996

[54] CATHETER PLACEMENT UNITS

[75] Inventor: Robert M. Wozencroft, Surbiton, England

[73] Assignee: Sterimatic Holdings Limited, Stroud, England

[21] Appl. No.: 211,226

[22] PCT Filed: Sep. 22, 1992

[86] PCT No.: PCT/GB92/01741

§ 371 Date: Mar. 25, 1994

§ 102(e) Date: Mar. 25, 1994

[87] PCT Pub. No.: WO93/05840

PCT Pub. Date: Apr. 1, 1993

[30] Foreign Application Priority Data

Sep. 25, 1991 [GB] United Kingdom .................. 9120416

[51] Int. Cl.$^6$ ............................................. A61M 5/00
[52] U.S. Cl. .......................... 604/171; 604/192; 604/198; 604/264; 604/280
[58] Field of Search .................. 604/198, 192, 604/197, 93, 162, 171, 110, 264, 280

[56] References Cited

U.S. PATENT DOCUMENTS

| 4,790,828 | 12/1988 | Dombrowski et al. |
| 4,950,252 | 8/1990 | Luther et al. |
| 4,994,041 | 2/1991 | Dombrowski et al. |
| 5,026,351 | 6/1991 | Dizon .................................. 604/264 X |
| 5,051,109 | 9/1991 | Simon |
| 5,176,655 | 1/1993 | McCormick et al. |
| 5,183,468 | 2/1993 | McLees ............................... 604/198 X |
| 5,279,591 | 1/1994 | Simon ................................. 604/192 X |
| 5,300,045 | 4/1994 | Plassche, Jr. ....................... 604/264 X |
| 5,348,544 | 9/1994 | Sweeney et al. .................... 604/198 X |

FOREIGN PATENT DOCUMENTS

WO90/08564 8/1990 WIPO.
WO91/01151 2/1991 WIPO.

*Primary Examiner*—Randall L. Green
*Assistant Examiner*—N. Kent Gring
*Attorney, Agent, or Firm*—Young & Thompson

[57] ABSTRACT

A catheter placement unit comprises an introducing needle (2) having a pointed tip (6) for introducing a catheter (4) into a desired position in a patient's body, a needle hub (3) for mounting the needle (2) so that the needle extends through an axial bore in the catheter (4) during introduction of the catheter into the patient's body and so that the needle can subsequently be withdrawn from the catheter bore leaving the catheter in position in the patient's body, and a needle tip protector (10) on the needle for shielding the needle tip (6) when the needle has been withdrawn from the catheter bore. The needle tip protector (10) includes a guard element (16) which is held against a resilient bias in a cocked position to one side of the catheter (4) while the catheter is introduced into the patient's body and which, on subsequent withdrawal of the needle (2) from the catheter bore, is moved laterally by resilient action from the cocked position into a guard position in which it shields the needle tip (6). Thus the protector (10) reliably guards against needle stick injuries during withdrawal and subsequent disposal of the needle.

10 Claims, 2 Drawing Sheets

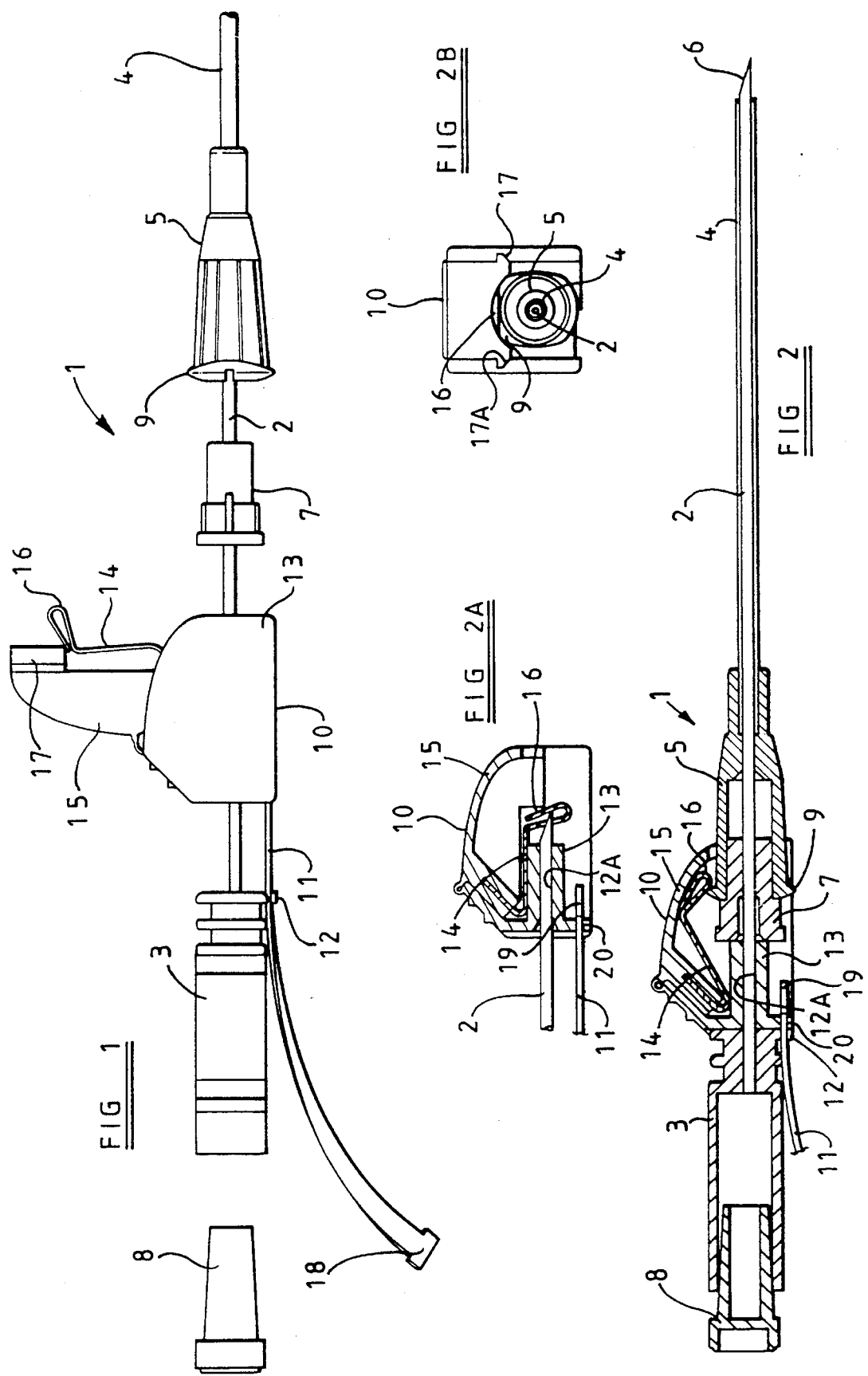

1

CATHETER PLACEMENT UNITS

FIELD OF THE INVENTION

This invention relates to catheter placement units.

BACKGROUND OF THE INVENTION

It is established medical practice to introduce a flexible tubular catheter into a desired position in a patient's body by means of a catheter placement unit which includes an introducing needle extending externally or internally of the catheter and projecting beyond the end of the catheter. In use of such a catheter placement unit to place a catheter within a patient's vein for supply of infusion fluid, for example, the needle tip projecting beyond the end of the catheter serves to puncture the patient's skin and to locate the catheter within the vein. When the catheter is suitably positioned, as may be determined by the flow of blood in the hub of the needle, the needle may be withdrawn leaving the catheter in position in the vein. Typically the needle is completely withdrawn from the catheter and safely disposed of prior to the connection of a fluid line to the catheter so as to prevent damage to the patient by the needle during infusion. However the need to withdraw the needle from the catheter leads to a risk that doctors or nurses will accidentally prick themselves with the needle, and this can be highly dangerous due to the risk of transfer of blood-related diseases.

U.S. Pat. No. 3,463,152 and U.S. Pat. No. 3,536,073 disclose catheter placement units of a type in which the needle is withdrawn into a housing connected to the catheter and locked therein after placement of the catheter in the patient's body, in order to prevent damage to the patient from the needle. However such catheter placement units are complex and bulky in that they require a needle housing which remains attached to the catheter in use, and are not suitable for use in applications where the needle is to be withdrawn completely from the catheter and disposed of.

U.S. Pat. No. 4,978,344 discloses a catheter placement unit of a type in which the needle is withdrawn completely from the catheter and disposed of after placement of the catheter in the patient's body, and in which the action of withdrawal of the needle from the catheter causes a tethered cap portion to be drawn over the needle tip. However the drawing of the cap portion over the needle tip relies on frictional engagement of the cap portion by the catheter hub, and it is possible to withdraw the needle from the catheter without triggering the required capping action. Also, because of the form of the capping portion, it is possible for the needle tip to be re-exposed after capping.

SUMMARY OF THE INVENTION

It is an object of the invention to provide a catheter placement unit with means to reliably prevent needle stick injuries on withdrawal of the needle.

According to the present invention there is provided a catheter placement unit as defined by the accompanying claims.

Since movement of the guard element into the guard position in use of such a catheter placement unit occurs as a direct consequence of withdrawal of the needle from the catheter bore, it follows that the needle tip is reliably protected by the guard element as soon as it is withdrawn from the catheter bore, and there is no risk of the doctor or nurse or the patient being accidentally pricked by the needle after withdrawal. Furthermore the needle may be safely disposed of without any additional shielding measures being required.

BRIEF DESCRIPTION OF THE DRAWINGS

Although the catheter placement unit may be supplied for fitting to a separately supplied assembly comprising a catheter and catheter hub, it is contemplated that the catheter placement unit supplied will generally include a catheter and catheter hub to which the needle, needle hub and protector are fitted ready for introduction of the catheter into the patient's body.

In order that the invention may be more fully understood, reference will now be made, by way of example, to the accompanying drawings, in which;

FIG. 1 is a side view of a catheter placement unit in accordance with the invention in a partially disassembled condition;

FIG. 2 is an axial section through the catheter placement unit of FIG. 1 when fully assembled, FIG. 2A showing a detail of the unit in the guard position and FIG. 2B showing an end view of the unit.

DETAILED DESCRIPTION OF THE INVENTION

Figure 3:
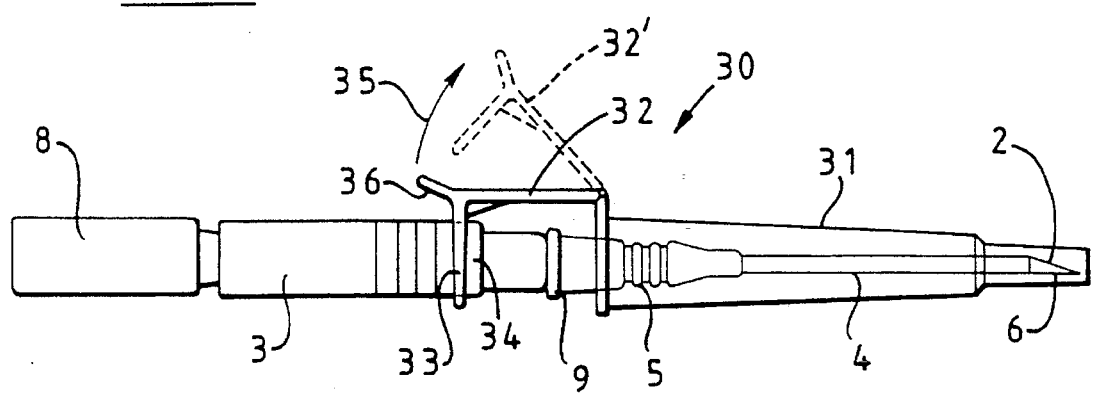
FIGS. 3 and 4 are side views of further catheter placement units in accordance with the invention.

Referring to FIGS. 1 and 2, the catheter placement unit 1 comprises an introducing needle 2 mounted on a transparent plastics needle hub 3 in conventional manner, and a flexible tubular catheter 4 mounted on a plastics catheter hub 5 in conventional manner. The needle 2 extends within the catheter bore so that its pointed tip 6 projects from the end of the catheter 4. A plug 7 is optionally fitted into the end of the catheter hub 5 for guiding the needle 2 within the catheter hub 5, although it is possible for this plug 7 to be omitted if the other parts of the assembly are suitably adapted. A vent filter 8 is fitted into the end of the needle hub 3, in conventional manner. Furthermore an annular flange 9 is provided on the end of the catheter hub 5.

In addition the catheter placement unit 1 includes a needle tip protector 10 on the needle which is coupled to the needle hub 3 by a flexible plastics strap 11 slidingly extending through an apertured part 12 of the needle hub 3. The protector 10 is positioned between the needle hub 3 and the catheter hub 5 with the needle 2 extending through a bore 12A in a plastics body part 13 of the protector 10, and a resilient guard element 14 made of spring steel is mounted on the body part 13 by a tensioning part 15. As shown in FIG. 2, when the unit is fully assembled the tensioning part 15 holds a bent end portion 16 of the guard element 14 in engagement with the annular flange 9 on the catheter hub 5 so as to retain the guard element 14 under tension in a cocked position against the resilient bias imparted by the spring steel. The tensioning part 15 is hingedly connected to the body part 13 and is pivotable from an initial position (as shown in FIG. 1) during assembly into its tensioning position (shown in FIG. 2) in which it is held by projections 17 which engage by snap action within corresponding recesses 17A (shown in FIG. 2B) in the body part 13.

In use of the catheter placement unit 1 to position a catheter within a patient's vein, the patient's skin is punctured by the needle tip 6 and the unit 1 is manipulated to place the needle tip 6 in the required position as indicated by the presence of blood in the needle hub 3. When the correct position is reached, the needle 2 is slowly withdrawn from the catheter bore by grasping the catheter hub 5 in one hand whilst the needle hub 3 is moved by the other hand in the direction away from the catheter hub 5 and the protector 10, the flexible strap 11 sliding within the apertured part 12 to permit such movement. When the needle hub 3 has been moved to a sufficient extent for the needle tip 6 to be withdrawn from the catheter hub 5 and the plug 7, the needle 2 and the needle hub 3 become detached from the catheter 4 and the catheter hub 5, and the guard element 14 is disengaged from the annular flange 9 on the catheter hub 5 to permit it to move by resilient action into its guard position protecting the needle tip 6, as shown in the detail of FIG. 2A.

Retention of the protector 10 on the needle 2 in this position is ensured by the strap 11 which is prevented from further sliding within the apertured part 12 by virtue of a stop 18 on the end of the strap 11. The other end of the strap 11 is also preferably provided with a stop 19 and is connected to the body part 13 of the protector 10 by extending through a slot 20 in the body part 13. It is convenient for the slot 20 and the corresponding slot in the apertured part 12 to have openings by means of which the strap 11 may be introduced into the slots from one side during assembly.

FIG. 3 shows a catheter placement unit 30 which is generally similar to the catheter placement unit 1 of FIGS. 1 and 2 except that it does not include the needle tip protector 10 and that it additionally includes a protective cap 31 for the needle 2 and catheter 4. The protective cap 31 is held on the unit 1 by a pivoting member 32 having fingers 33 which engage flange formations 34 on the needle hub 3. In order to disengage the protective cap 31 from the unit 30, the pivoting member 32 is simply pivoted in the direction of the arrow 35 by exerting a pushing force on a projecting flange 36 so as to place the pivoting member 32 in the position shown in broken lines at 32' clear of the formations 34 on the needle hub 3 so that the protective cap 31 may simply fall away. This avoids the risk of needle stick associated with conventional arrangements due to the need for the user's hand to be placed in the vicinity of the needle tip when removing the protective cap.

Figure 4:
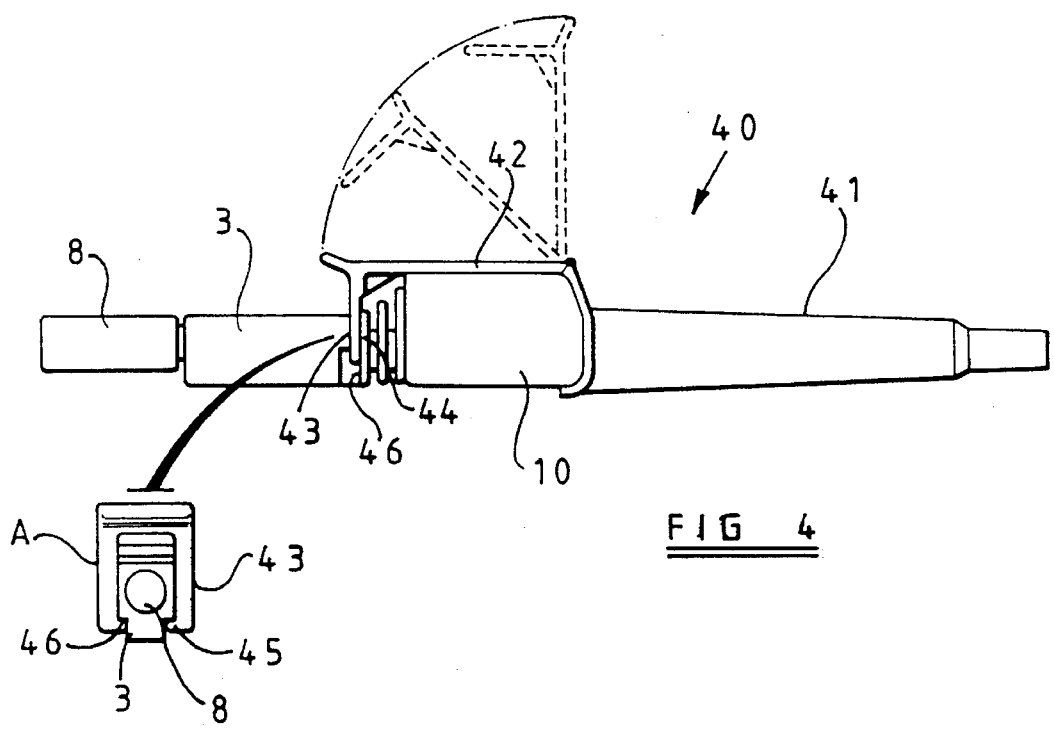

FIG. 4 shows a catheter placement unit 40 both with a needle tip protector 10 as described with reference to FIGS. 1 and 2 and a protective cap 41 mounted on the unit by a pivoting member 42 which is similar to the pivoting member 32 of FIG. 3 except that it is adapted to extend over the protector 10 and to engage flange formations 44 on the needle hub 3 by means of fingers 43. FIG. 4 includes at A an end view of the unit 40 showing the manner in which the fingers 43 extend on opposite sides of the needle hub 3 and include projections 45 which extend into recesses 46 in the needle hub 3. The manner in which such a protective cap 41 is disengaged from the unit 40 to enable placement of the catheter in a patient's body is as previously described.

We claim:

1. A catheter placement unit comprising a catheter (4) having an axial bore, a catheter hub (5) at one end of the catheter (4), an introducing needle (2) having a pointed tip (6) for introducing the catheter (4) into a desired position in a patient's body, a needle hub (3) at the end of the needle (2) remote from the tip (6) for mounting the needle (2) so that it extends through the catheter bore for introduction of the catheter into the patient's body and so that it can subsequently be withdrawn from the catheter bore leaving the catheter in position in the patient's body, and a needle tip protector (10) on the needle (2) for shielding the needle tip (6) when the needle has been withdrawn from the catheter bore, the needle tip protector (10) including a guard element (14) which is held against a resilient bias in a cocked position to one side of the catheter (4) while the catheter is introduced into the patient's body and which, on subsequent withdrawal of the needle (2) from the catheter bore, moves laterally by resilient action from the cocked position into a guard position shielding the needle tip (6), the needle tip protector (10) obstructing movement of the catheter hub (5) along the needle (2) so as to prevent separation of the catheter (4) from the needle tip protector (10) until the needle (2) has been withdrawn from the catheter bore so as to thereafter trigger shielding of the needle tip (6).

2. A unit according to claim 1, wherein the protector (10) is arranged to obstruct movement of the catheter hub (5) along the needle (2) by means of a portion of the guard element (14) which, when the guard element (14) is in its cocked position, engages a flange (9) on the catheter hub (5) so as to obstruct movement of the flange (9) beyond said portion of the guard element (14).

3. A unit according to claim 1, wherein the protector (10) is coupled to the needle hub (3) by a flexible elongate member (11) permitting movement of the needle hub (3) away from the protector (10) to withdraw the needle (2) from the catheter bore.

4. A unit according to claim 3, wherein the flexible elongate member (11) is connected to the needle hub (3) by means of a sliding connection (12) permitting paying out of the flexible elongate member (11) between the needle hub (3) and the protector (10) until a stop (18) on the flexible elongate member (11) is reached.

5. A unit according to any claim 1, wherein the protector (10) includes a body part (13) having a bore (12A) extending therethrough for passage of the needle (2), the guard element (14) being mounted on the body part (13) so as to be movable between its cocked and guard positions.

6. A unit according to claim 1 wherein the guard element (14) is a resilient element which is held under tension in its cocked position and is moved into its guard position under its own resilience.

7. A unit according to claim 1 wherein the guard element (14) is fixed at one end and has a bent portion (16) at its other end for shielding the needle tip (6).

8. A unit according to claim 1 wherein the guard element (14) is mounted on a body part (13) of the protector (10) by a tensioning part (15) which is movable from an initial position permitting positioning of the protector (10) relative to the catheter to a tensioning position holding the guard element (14) under tension in its cocked position.

9. A unit according to claim 8, wherein the tensioning part (15) is hingedly connected to the body part (13) of the protector (10) so as to be pivotable from its initial position to its tensioning position.

10. A unit according to claim 1 wherein a removable protective cap (41) for shielding the needle tip (6) is coupled to the needle hub (3) by a coupling part (42) which is disengageable from the needle hub (3) by pivoting to effect removal of the protective cap (41).

* * * * *